(12) United States Patent
Einarsson et al.

(10) Patent No.: US 8,795,679 B2
(45) Date of Patent: Aug. 5, 2014

(54) PHARMACEUTICAL AND COSMETIC USE OF EXTRACTS FROM ALGAE OBTAINABLE FROM SALINE HOT WATER SOURCES

(75) Inventors: Sigurbjorn Einarsson, Reykjavik (IS); Asa Brynjolfsdottir, Kopavogur (IS); Jean Krutmann, Wegberg (DE)

(73) Assignee: Blaa Lonid Hf (IS)

( * ) Notice: Subject to any disclaimer, the term of this patent is extended or adjusted under 35 U.S.C. 154(b) by 1014 days.

(21) Appl. No.: 12/299,749

(22) PCT Filed: May 7, 2007

(86) PCT No.: PCT/IS2007/000012
§ 371 (c)(1),
(2), (4) Date: Mar. 25, 2009

(87) PCT Pub. No.: WO2007/129331
PCT Pub. Date: Nov. 15, 2007

(65) Prior Publication Data
US 2010/0028376 A1    Feb. 4, 2010

(30) Foreign Application Priority Data

May 5, 2006 (IS) .............................. 8442
May 10, 2006 (IS) .............................. 8449

(51) Int. Cl.
*A61K 36/02* (2006.01)

(52) U.S. Cl.
USPC .................................................. 424/195.17

(58) Field of Classification Search
None
See application file for complete search history.

(56) References Cited

U.S. PATENT DOCUMENTS 7,629,391 B2 * 12/2009 Jacquinot et al. ............... 516/81
2007/0003647 A1 * 1/2007 Jensen et al. .................. 424/780

FOREIGN PATENT DOCUMENTS

| FR | 2728467 | | 6/1996 |
| FR | 2795959 | | 1/2001 |
| GB | 002301587 A | * | 12/1996 |
| JP | 356063911 A | * | 5/1981 |
| JP | 2001269180 A | | 10/2001 |
| JP | 02004027041 A | * | 1/2004 |
| WO | 2005007126 A | | 1/2005 |

OTHER PUBLICATIONS

Romay (Antioxidant and anti-inflammatory properties of C-phycocyanin from blue-green algae, Inflamm.res. 47(1998) pp. 36-41).*
"Blue Lagoon Iceland" Internet Citation, [online] 2004, XP002298084 Retrieved from the Internet: URL:http://www.bluelagoon.com/top_en/About_Blue_Lagoon/>[retrieved on Sep. 3, 2009].
[Online] 2004, XP002500756 Retrieved from the Internet: URL:http://web.archive.org/web/20041209080510/www.bluelagoon.com/Dermatology_Clinic/Psoriasis_Treatment/> [retrieved on Oct. 22, 2008].
[Online] 2004, XP002500757 Retrieved from the Internet: URL://http://web.archive.org/web/20041205010811/bluelagoon.com/Dermatology_Clinic/Treatment_products/How_to_use/> [retrieved on Oct. 22, 2008].
[Online] 2004, XP002500758 Retrieved from the Internet: URL:http://web.archive.org/web/20041204071314/www.bluelagoon.com/shop/en/category.as px?ID=Face> [retrieved on Oct. 22, 2008].
PCT/IS2007/000012 International Search Report dated Dec. 11, 2008.
Petursdottir, Solveig K. et al. "Analysis of the unique geothermal microbial ecosystem of the Blue Lagoon." FEMS Microbiol. Ecol. 70 (2009) 425-432.

* cited by examiner

*Primary Examiner* — Chris R Tate
*Assistant Examiner* — Randall Winston
(74) *Attorney, Agent, or Firm* — Quarles & Brady LLP (57) ABSTRACT

The invention provides the use of extracts from algae for cosmetic and/or medical treatment of skin, including improving and enhancing the skin-barrier, anti-aging treatment and photo-protective treatment. The invention is based on the finding that extracts from algae obtainable from saline hot water sources exhibit a multi-faceted biological effect useful in the cosmetic and/or therapeutic treatment of skin for the above purposes. Specifically, it has been shown that such algae extracts induce markers (involucrin, filaggrin and transglutaminase-1) for skin barrier formation in keratinocytes, induce collagen expression in dermal fibroblasts and inhibit UVA-induced up-regulation of photo-aging markers (matrix metalloproteinase MMP-1 and cytokine IL-6).

21 Claims, 4 Drawing Sheets

FIG. 1 a) Induction of Markers of Differentiation Algae Extract Sample 1 8.3µg/ml b) Induction of Markers of Differentiation Algae Extract Sample 1 4.2µg/ml c) Induction of Markers of Differentiation Algae Extract Sample 1 1.7µg/ml d) Induction of Markers of Differentiation Algae Extract Sample 1 0.8µg/ml

FIG. 2 a)

Induction of Markers of Differentiation
Algae Extract Sample 2 8.3µg/ml b)

Induction of Markers of Differentiation
Algae Extract Sample 2 4.2µg/ml c)

Induction of Markers of Differentiation
Algae Extract Sample 2 1.7µg/ml d)

Induction of Markers of Differentiation
Algae Extract Sample 2 0.8µg/ml

PHARMACEUTICAL AND COSMETIC USE OF EXTRACTS FROM ALGAE OBTAINABLE FROM SALINE HOT WATER SOURCES

FIELD OF INVENTION

The present invention is within the field of cosmetics and cosmetically effective ingredients, and specifically concerns the use of algae, in particular blue-green algae, from saline hot water sources for cosmetic and/or medical treatment of skin.

TECHNICAL BACKGROUND AND PRIOR ART

There is a growing interest in natural ingredient beauty products and products that prevent and reduce aging symptoms as well as products that can protect the skin from various environmental stress. A multitude of components from various sources have been used in cosmetic products, although evidence of beneficial effects of individual components is in some cases very limited.

Algae, both macroalgae ("sea weed") and microalgae, have been used in cosmetic products as thickening agents, water-binding agents, and antioxidants. Certain macroalgae, such as Irish moss and carrageenan, are used as a source of natural proteins, vitamin A, sugar, starch, vitamin B1, and minerals including iron, sodium, phosphorus, magnesium, copper, and calcium. Algae typically found in cosmetics include *Ulva lactuca, Ascophyllum, Laminaria longicruris, Laminaria saccharine, Laminaria digitata, Alaria esculenta*, various *Porphyra* species, *Chondrus crispus*, and *Mastocarpus stellatus*. Microalgae have as well been used in cosmetic compositions, these include *Chlorella, Spirulina, Dunaliella* and *Odontella* species.

U.S. patent application published as U.S. 2005/0123499 A1 discloses a cosmetic composition comprising at least two of the following ingredients: algae extract, sea fennel and *Codium Tamentosum* extract. A specific example contains a mixture of a Chlorella extract sold under the trade name CHLORELLINE®, an extract obtained from Ulva Lactuca sold as AOSAINE®, and a green flower extract obtained from *Monostroma*. Other cosmetic products which comprise algae are disclosed in published patent applications FR 2834886A, JP2004051568A2, JP 2005047860A2, FR 2838340A, FR 2838341A, FR 2838342A, FR 2806906A, FR 2850277A, FR2796556A, JP11228437A and JP005415A.

Although the mechanism behind skin aging is not completely understood, the cosmetic market offers an enormous variety of anti-aging products. Most of the products available are directed to the mechanisms of stimulating collagen and glycosaminoglycan synthesis by fibroblasts in the epidermis, lowering free radical levels in the skin or increasing firmness and flexibility of the stratum corneum.

Skin Barrier Enhancement

The skin barrier, also referred to as the epidermal permeability barrier, protects against infection and poisoning, prevents desiccation and is essential for terrestrial life. Barrier function is conferred by the outer layer of epidermis, the stratum corneum which consists of dead, keratin-filled cells embedded in a lipid matrix. Stratum corneum is formed from granular layer keratinocytes during terminal differentiation of normal adult epidermis. A rapid aggregation of the keratin cytoskeleton, which causes a collapse of the granular cells into flattened a nuclear squames, is a key step in formation of the outermost barrier layer of the skin. This condensed cytoskeleton is cross linked by transglutaminases during formation of the cornified cell envelope (CE). Transglutaminases are expressed and activated during terminal differentiation of keratinocytes. The membrane-bound form of the transglutaminase-1 forms ester bonds between specific glutaminyl residues of human involucrin during formation of the cornified cell envelope enzyme. The CE not only prevents water loss but also impedes the entry of allergens and infectious agents. During the last stage of its terminal differentiation of keratinocytes is the formation of a cross linked envelope. This envelope is made up of membrane and cytosolic proteins cross linked by glutamyl lysine isopeptide bonds. Involucrin, being a keratinocyte protein which appears first in the cytoplasm and later becomes cross linked to membrane proteins by transglutaminase, is the most abundant component is of the envelope. Loricrin is another major component of the cross linked cell envelope of the epidermis of the skin, also known as the cornified cell envelope (CE). Filaggrin is a protein which is expressed in granules in the granular layer of interfollicular epidermis which is predominantly composed of the protein pro-filaggrin. Upon terminal differentiation of granular cells, pro-filaggrin is proteolytically cleaved into filaggrin peptides. Filaggrin aggregates the keratin cytoskeleton and is therefore a key protein in facilitating epidermal differentiation and maintaining barrier function.

Agents that enhance and improve the natural skin barrier function as described above are useful in cosmetic products, e.g. for improving retention of moisture in the skin, lessening dry skin formation and for generally keeping the skin in a healthy and visually appealing condition.

Anti-Aging Effect by Induction of Collagen Synthesis

Medical research has demonstrated that a cause of wrinkle formation is induction of MMP-1 expression due to photoaging leading to collagen degradation, which cannot be compensated by a concomitant induction of collagen synthesis (Scharfetter et al., 1991). This imbalance is further increased by the fact that UVA irradiation results in a decreased expression of Collagen 1A1 and Collagen 1A2 (Südel et al., 2005). The transcription factor AP1 is activated upon UVA stimulation and exerts the induction of MMP-1 and the repression of Collagen 1A1 and Collagen 1A2 (Chung et al., 1996). Hence, agents that stimulate collagen synthesis and preferably as well inhibit photo-induced up-regulation of MMPs would be very beneficial in cosmetically active skin-care products to provide an anti-aging effect.

The term "skin aging" relates generally to the thinning and/or general degradation of the dermis. This involves a decrease in collagen gene expression, lower fibroblast activity and fibroblast regeneration as well as shrinking of the lamellar barrier, which is shown in the inability of the skin to retain moisture. Accordingly, the term "anti-aging" as used herein refers to an effect which counteracts skin aging, i.e., acts against the above effects for retaining smooth and healthy skin.

Photoaging and Photo-Protection of Skin

Exposure of human skin to ultraviolet (UV) light induces multiple deleterious effects in the epidermis and dermis. UVB (290-320 nm) radiation primarily causes photo carcinogenesis due to its direct interaction with cellular DNA and subsequent formation of cyclobutane pyrimidine dimers, 6-4 photoproducts and thymine glycols. The major consequence of UVA (320-400 nm) radiation is the generation of reactive oxygen species, which, however, can also induce cancer, e.g. by generation of oxidized DNA base derivatives like 8-hydroxydeoxyguanosine.

Whereas UVB effects are mainly restricted to the epidermis, UVA rays directly effect the dermal compartment and are therefore thought to be the major factor responsible for photoaging of human skin. It has been shown that especially the long wave part of UVA referred to as UVA1 (340-400 nm) accounts for damaging effects in human dermal fibroblasts, through induction of cytokines, matrix metalloproteinases and mitochondrial DNA mutations. Of these, the induction of collagenase (matrix metalloproteinase-1, MMP-1) which degrades collagen type I, the major constituent of the connective tissue, is of particular significance since the extent of collagen I reduction correlates with photo damage in human skin. It has been postulated that the UVA1-induced up-regulation of MMP-1 is regulated by interrelated autocrine loops of interleukin-1 (IL-1) and interleukin-6 (IL-6); UVA1 radiation rapidly induces bioactivity of extracellular IL-1α and IL-1β which then induce IL-6 expression. IL-1 and IL-6 both enhance the biosynthesis of MMP-1, peaking at 24 h. concomitantly; the de novo synthesis of IL-1 is stimulated leading to a further boost of IL-6 and MMP-1 induction. Consequently, induction of MMP-1 is a useful marker for skin aging. UVA-induced up-regulation of the cytokine IL-6 has previously been shown to be a prerequisite of UVA-induced MMP-1 induction. Therefore, agents that reduce the photo-induced up-regulation of MMPs are potentially very useful for photo-protection by reducing and/or slowing down photoaging.

SUMMARY OF INVENTION

The present inventors have found that microalgae which are found abundantly in specific mineral-rich and/or saline geothermal sources (preferably at a temperature in the range of about 30-50° C.) can be used as sources for pharmaceutically/cosmetically active ingredients. Specifically, as disclosed herein, extracts from such algae exhibit measurable activity in terms of enhancing skin barrier function, anti-aging treatment by inducing de novo collagen formation and providing effective photo-protective effect (reducing photoaging effects of UV light).

As the Examples herein illustrate two taxonomically quite different miroalgae species from said environment exhibit this described biological effects. From this it can be inferred that the effects relate to the common denominator of the microalgae species, which is the ability to thrive in these special and harsh environmental conditions.

In a first aspect, the invention provides an extract derived from algae obtainable from hot mineral-rich and/or saline water environment for use in a pharmaceutical and/or cosmetic product.

In another aspect, the invention provides the use of an extract derived from algae obtainable from hot mineral-rich and/or saline water environment for the manufacture of a pharmaceutical and/or cosmetic product for enhancing skin barrier function and/or anti-aging through enhancing collagen formation and reducing photoaging of the skin of a mammal.

In a further aspect, the invention provides a cosmetic and/or pharmaceutical composition comprising a ruptured cell extract from algae obtainable from a hot mineral-rich and/or saline water source and one or more cosmetically acceptable carrier or diluents.

DETAILED DESCRIPTION OF THE INVENTION

The algae which can be used in accordance with the present invention are readily obtainable and grow abundantly in mineral-rich and/or saline hot water conditions. As can be understood from the description herein microalgae are preferred for the purpose of the invention, these can be both eukaryotic and prokaryotic microalgae. Eukaryotic microalgae include members of the group referred to as green algae, which include unicellular and colonial flagellates, usually but not always with two flagella per cell, as well as various colonial, coccoid, and filamentous forms. Useful prokaryotic algae comprise the group generally referred to as blue-green algae also referred to as cyanophytes and belong the class of cyanobacteria. The blue-green algae have a prokaryotic cell structure and conduct photosynthesis directly within the cytoplasm, rather than in specialized organelles. Some filamentous blue-green algae have specialized cells, termed heterocysts, in which nitrogen fixation occurs.

Microalgae used in the invention can be of unicellular or multicellular forms (e.g., colonial, filamentous, mats, and the like). The individual cells themselves can be of generally coccoid, rod-like or other shape. The specific algae species used in the examples incorporated herein are collected from a geothermal basin in Iceland ("Blue Lagoon", Svartsengi) with water originating from underground reservoirs filled with geothermal seawater. The salinity of the geothermal seawater indicates that it is composed of 65% seawater and 35% freshwater. The lagoon water has an average temperature of about 37° C., with local and seasonal variations in the range of about 30-45° C., a pH of about 7.5 and a salt content of 2.5 wt %. It can be assumed that algae such as are disclosed in the specific examples herein can be readily grown under corresponding conditions, either in other geothermal geographic locations or in simulated non-natural settings.

The cells of the algae are preferably ruptured to release active components from within the cells. This can be accomplished with several different methods well known to the skilled person, although algal cells useful in this context may be relatively rigid and may need forceful methods for cell rupture. A preferred method comprises grinding in a mixture with alumina ($Al_2O_3$), silica or ceramic particles (e.g., in a mortar or bead mill) and subsequently extracting from the alumina/silica solid. Other methods may however as well be used, such as osmotic shock, autolysis, mixer mill and the like.

Skin Barrier Enhancement

It has surprisingly been discovered, as is disclosed in the Examples herein, that an algae extract as defined above can enhance skin barrier function, as clearly indicated by experimental data where extracts from algae extracts according to the invention are shown to induce markers for barrier formation, such as those mentioned above, in cultured human keratinocytes.

Induction of Collagen Synthesis

The effect of algae extracts of the invention on the induction of Col1A1 and Col1A2 expression in human dermal fibroblasts using real time RT-PCR has been verified. Both tested algae extracts showed a dose dependent expression increase of the collagen genes with a 2- to 3-fold expression at 2 μg/mL, as described in more detail in the Examples below.

Photoaging Effect

As mentioned above, ultraviolet exposure of human skin induces multiple deleterious effects in the epidermis and dermis. Induction of MMP-1 is often used as an indicator for skin aging, and consequently, agents that reduce the photo-induced up-regulation of MMP are potentially very useful for reducing and/or slowing down photoaging.

As the Examples below clearly show, extracts according to the invention, as illustrated by two taxonomically quite different saline hot water blue-green algae, have a significant effect on the down-regulation of MMP-1 in cultured human dermal fibroblasts upon UV irradiation. The positive results from these two quite different species indicate that the beneficial features rendering the measured effects to the cell extracts are not isolated to these particular species, but rather relate to the harsh conditions under which they grow, common to both species, and the physiological evolutionary adjustment these species have undergone in order to thrive in this special environment.

Preferred Materials and Compositions

The present invention describes cosmetic and/or pharmaceutical compositions for topical applications for enhancing skin barrier function, providing an anti-aging effect through enhancing collagen formation and reducing photo-aging of the skin. Preferred embodiments of the preparations of the invention are further distinguished as natural products obtainable from saline geothermal environment.

In the present context the term "topical application" relates to directly laying on or spreading on outer skin. The term "cosmetic" or "cosmetic composition," according to the invention is intended to include all types of products that are applied in any manner directly to the skin for the purpose of affecting the general visual appearance of the skin. The amount of the cosmetic composition, according to the present invention, to be applied to the skin and the duration or number of applications can be determined easily on an individual basis by utilizing the cosmetic composition until a visible improvement of the outer surface of the skin results.

In an embodiment of the present invention the extract of the present invention is derived from algae obtainable from saline hot water environment for use in a pharmaceutical and/or cosmetic product. The algae are suitably collected from a natural source or grown under suitable conditions, isolated, and cells of said algae are preferably ruptured to obtain said extract. Algae to be used according to the invention preferably have an optimal growth temperature in the range of 30-70° C., more preferably in the range of 30-50° C. In some embodiments algae of the present invention comprise blue-green algae (cyanobacteria) type, such as but not limited to coccoid and filamentous shaped bacteria, which can be unicellular, colonial, or filamentous.

The algae extracts obtainable from saline geothermal environment as disclosed herein can be mixed with a cosmetically and/or pharmaceutically acceptable carrier to form a cosmetic or pharmaceutical composition, which can be topically applied to skin. The composition can be applied to the skin in cosmetically; biologically or therapeutically effective amounts over a period of time sufficient to result in repair or remodelling of the dermis. This repair or remodelling will typically be apparent from a visible improvement of the appearance of the outside of the skin. However, application of the product may also have as a primary desired effect to reduce premature aging and wear of the skin, e.g. photoaging.

The pharmaceutical and cosmetic compositions according to the invention may include but are not limited to, in addition to a component of algae extracts as described herein, conventional ingredients and carriers used in cosmetic or pharmaceutical products. Said composition may take the form of a fatty or non-fatty cream, a milky suspension or emulsion of the water-in-oil or oil-in-water type, a lotion, a gel or jelly, a colloidal or non-colloidal aqueous or oily solution, a paste, a soap, a foam, an anhydrous base including a powder, an ointment, a semi-soluble or dispersible tablets (to be dissolved/suspended in a fluid, such as water) or sticks.

In the present context the term "cream" used herein is meant to encompass all cosmetic cream-type materials which include, for instance, hand creams, cleansing creams, milky lotions, cold creams, vanishing creams, hair creams, foundation creams, beauty washes, facial packs and the like.

The amount of active ingredient contained in the compositions of the present invention may vary between wide limits, depending upon the formulation and the frequency of use of said compositions. Generally, said compositions can contain from 0.01%-99% by weight of the algae extracts obtained from saline geothermal environment but more typically compositions will contain in the range of about 0.01-2.5 wt % of the algae extract, such as in the range of about 0.05-2.5 wt % and more preferably the range of 0.05-0.5 wt %, e.g. in the range of about 0.1-0.5 wt %. The composition may contain an extract from a single algae species or an extract from two or more species such as comprising either or both of the species which are specifically disclosed herein.

The compositions according to the invention can also contain conventional vehicles or carriers, such as solvents, fats, oils and mineral waxes, fatty acids and derivatives thereof, alcohols and derivatives thereof, glycols and derivatives thereof, glycerol and derivatives thereof, sorbitol and derivatives thereof, surface-active agents of the anionic, cationic or non-ionic type, emulsifying agents, preserving agents, perfumes, etc.

As mentioned above the invention also relates to pharmaceutical compositions comprising algae extracts according to the invention and the use of algae extracts of the invention in the manufacture of medicaments for therapeutic treatment of diseases, disorders and conditions which respond to the therapeutic effect disclosed herein. These pharmaceutical compositions may be used in the treatment of skin conditions such as skin damage due to corticoid steroids, skin atrophy, structural weakness of the connective tissue, wound healing and atophic dermatitis, eczema, psoriasis, rosacea and other skin diseases.

In an embodiment of the present invention the use of an extract as described herein for the manufacture of a pharmaceutical and/or cosmetic product is provided for enhancing skin barrier function, providing an anti-aging effect through enhancing de novo collagen formation in the skin and/or reducing photoaging of the skin of a mammal, including a human.

As illustrated with the accompanying Examples, the biological effect of the extracts of the invention enhancing skin barrier function, inducing collagen formation and reducing photoaging, can be measured by monitoring several biomarkers such as, respectively for the mentioned activities:

induction of involucrin, transglutaminase-1, filaggrin and loricrin in human keratinocytes, induction of Col1A1 and Col1A2 expression in human dermal fibroblasts, and up-regulation of MMP1 in human dermal fibroblasts upon UV irradiation.

The monitoring of the biomarkers can be monitored by following the gene expression of these markers using methods such as, but not limited to microarrays and RT-PCR. The monitoring of the biomarkers can further be monitored by measuring protein levels using methods such as, but not limited to immunoassay including ELISA, RIA, EIA and FACS analysis etc, or mass spectrometry including protein microarrays and immunohistochemistry methods.

In an embodiment of the present invention a cosmetic and/or pharmaceutical composition is provided comprising a ruptured cell extract from algae such as described above and one or more pharmaceutically and/or cosmetically acceptable carrier or diluent. The cosmetic composition according to the embodiment can be of any such type as is mentioned herein above.

In certain embodiments algae of the present invention comprise either or both *Cyanobacterium* sp. deposited with the Culture Collection of Algae and Protozoa SAMS Research Services Ltd. United Kingdom, under accession numbers CCAP 1483/1 and CCAP 1483/1, with Applicant's identification reference identification BLICE-0405-01 and BLICE-0405-02, respectively.

Also, in some useful embodiments the algae used in the invention can be characterised by their 16S rRNA sequences, i.e. the RNA sequence of the 16S domain of ribosome. The 16S rRNA gene has been used as a molecular marker, enabling the phylogenetic assignment of the organisms from which it originated. The 16S rRNA sequences of the two algae species which are used in the accompanying Examples have been sequenced. The 16S rRNA sequence of the coccoid algae species identified as BLICE-0405-01 is shown as SEC ID NO: 19 and the 16S rRNA sequence of the filamentous algae species identified as BLICE-0405-02 is shown as SEC ID NO: 20.

Consequently, in useful embodiments of the invention, the algae extracts used as described herein and products comprising such extracts comprise algae from one or more algae species from the group of species having a 16S rRNA sequence which is shown as SEQ ID NO: 19, a 16S RNA sequence which is shown as SEQ ID NO: 20 and species belonging to the same phylogenetic families, for example species with substantially similar 16S rRNA sequences.

Combinations of Algae Extract and Silica

Applicant's co-pending international application titled "Pharmaceutical and cosmetic use of silica" and corresponding IS application 8448 filed on 5 May 2006, which are hereby incorporated in full by reference, disclose that silica in suitable form has a biological effect beneficial in skin products, as demonstrated with corresponding assays as are described in the present application. Silica is the general term for silicon dioxide ($SiO_2$) which is found in nature in several forms and can also be synthesised by precipitating silicious acids and by processes based on acid leaching of silicious minerals. The preferred silica material according to the invention is natural silica mud precipitated from geothermal saline sources, such as the Blue Lagoon geothermal basin in Iceland ("Blue Lagoon", Svartsengi) mentioned above. As hot underground water reaches the ground surface its temperature and pressure drops leading to silica precipitation, forming a white colloidal mud-like substance with a high salt content, which is referred to herein as "silica mud".

Accordingly, silica as described in the mentioned application can be added to formulations of the present invention to enhance further the beneficial effect documented herein. The silica can be incorporated in any forms of products as are described above, in a suitable concentration, such as within the range of about 0.01-99% and preferably the range of 0.01-10% and more preferably in the range of about 0.05-2.5 wt %, such as in the range of about 0.05-1.0 wt % and more preferably in the range of about 0.05-0.50 wt %, such, as e.g. about 0.10 wt %, about 0.20 wt % or about 0.25 wt % or about 0.30 wt %.

Consequently, the present invention provides formulations comprising an extract from one or more algae species such as those mentioned herein in combination with biologically active silica. The formulations are suitable as cosmetic or pharmaceutical products. The invention also encompasses the use of such combinations for the manufacture of a medicament, preferably for treatment or prophylaxis of any disease, disorder and condition which responds to the therapeutic effect disclosed herein (e.g. for any of the above mentioned indications).

Accordingly, the invention further relates to a method for enhancing the natural skin barrier function of the skin of a mammal including a human comprising applying to said skin a cosmetic composition with a skin barrier function enhancing amount of a combination of an algae extract and silica as described herein. The method is particularly set forth as a cosmetic method, i.e. a method for affecting the visual appearance of the skin. The cosmetic composition is suitably selected from any of the conventional types of topical cosmetic formulations such as those described herein above.

In a further aspect, the invention provides a cosmetic method for reducing photoaging of the skin of a mammal such as a human, comprising applying to said skin a cosmetic composition preferably such as described above, with a photoprotective amount of combination of an algae extract and silica as described herein, preferably formulated as described herein above.

In a further aspect a method is provided for reducing a skin-aging effect of the skin of a mammal comprising applying to said skin a cosmetic composition with an anti-aging effective amount of combination of an algae extract and silica as described herein. As is understood from the description set forth above, the anti-aging effective amount of said combination preferably induces collagen formation in the skin as can be assessed with methods described in the Examples disclosed.

For the use in accordance with the present invention, silica mud as described above may be suitably further purified, by removing coarse particles, rinsing and washing. The marine type salts, (mainly NaCL, KCl and $CaCl_2$) will not be completely rinsed from the material, hence the material will have a significant salt content, which is, however, not considered detrimental and is in fact believed to be advantageous. In certain cosmetic products coarse particles may however be desired and in such cases finer particles can be separated out to give a higher ratio of coarse material (agglomerates).

The above aspects and embodiments relate as well to silica in any other cosmetically suitable form from other and preferably more conventional sources, e.g. silica from diatoms, refined diatomaceous earth (kieselguhr), colloidal silica in the form a mud-like material or suspension, precipitated silica such as produced from sodium silicate solutions and acid and/or by dissolution of silicate minerals, also various forms of silicic acids may as well be used for the invention, for use as solutions (e.g. super-saturated solutions) or for precipitating silica.

Commercially available colloidal silica has been tested and as is documented herein, such material exhibits significant activity in all the employed activity assays.

Also, the precipitated geothermal silica mud can be simulated with other forms of silica by admixing the characteristic salts in appropriate amounts to silica in a suitable form.

Description of Silica

The silica which is suitable for use in accordance with the invention will generally have material properties typical for precipitated silica, such as with respect to particle size distribution, specific surface area and porosity. It should be noted that the parameters can be affected by treating silicious material to obtain silica with desired material properties depending on the intended application and formulation. Consequently, in useful embodiments the silica used in the invention will have a BET specific surface are in the range of about 10-200 $m^2/g$, such as in the range of about 10-100 $m^2/g$ including the range of 20-100 $m^2/g$ or the range of 10-50 $m^2/g$ but not limited to those particular ranges, as long as the material exhibits the desired biological properties as exemplified herein. Particle size of silica for use in the invention can vary and the particle size can be affected by treating silica material, e.g. by ultrasound, in order to break up agglomerates into smaller particles. Accordingly silica used as described herein may have a particle size d50 (µm) value in the range from about 2 µm to about 75 µm, such as in the range of 4-50 µm, e.g. in the range of about 4-25 µm or the range of about 10-50 µm. The particle size distribution can be narrow or wide, such as having a d90 value anywhere in the range of about 10-350 µm, where depending on the desired product texture characteristics, the silica can be selected and/or treated to have a generally coarse particle size or a generally fine particle size.

The tested silica mud significantly induced expression of the differentiation markers involucrin, filaggrin and transglutaminase-1, especially at the early time point (24 h post addition of the tested substance). The second tested silica sample (sodium metasilicate) showed as well substantial up-regulation.

The effect of silica on the induction of Col1A1 and Col1A2 expression in human dermal fibroblasts using real time RT-PCR has been verified. The tested silica mud showed a dose dependent expression increase of the collagen genes with a maximal 2-fold expression at 10 µg/mL.

As tested by two different samples from different natural sources, has a significant effect on the down-regulation of MMP-1 in cultured human dermal fibroblasts upon UV irradiation. Silica mud provided by Blue Lagoon inhibited dose-dependently the up-regulation of both IL-6 and MMP-1. Similar results were observed for a control substance sodium metasilicate.

The results from the two different types of silica indicate that the beneficial features rendering the measured effects to the material are not isolated to silica precipitated from saline geothermal sources and clearly show that silica inhibits dose-dependently UVA-induced up-regulation of both markers IL-6 and MMP-1.

EXAMPLES

Example 1

Preparation of Extract from Coccoid Saline Hot Water Blue-Green Algae

Algae of the type designated as BLICE-0405-01 were collected from culture tanks, washed three times in phosphate buffer saline, allowed to settle and decanted. The cells were added to two parts alumina ($Al_2O_3$) particles (Sigma, A 2039 Alumina) in a mortar, grinding with pestle as long as the mass makes a smacking noise. Extracts were centrifuged (1 hour, 20.000×g, 4° C.). This extract is referred to below as Extract 1 or Sample 1.

Example 2

Preparation of Extract from Filamentous Saline Hot Water Blue-Green Algae

Algae of the type designated as BLICE-0405-02 were collected from culture tanks and prepared essentially as described in Example 1. This extract is referred to below as Extract 2 or Sample 2.

Example 3

Induction of Differentiation in Human Epidermal Keratinocytes by Algae Extracts

The effect of the extracts obtained in Examples 1 and 2 on the differentiation markers involucrin, transglutaminase-1, filaggrin, and loricrin in human epidermal keratinocytes has been assessed. As control a ceramide mix (10 µM) was used to induce the differentiation markers.

Materials and Methods

Long term cultured normal human epidermal keratinocytes, NHEK, prepared from neonatal foreskin are cultured in Keratinocyte SFM (Invitrogen, Heidelberg, Germany) supplemented with bovine pituitary extract (Invitrogen, Heidelberg, Germany) and recombinant epidermal growth factor (Invitrogen, Heidelberg, Germany). Cells are propagated up to passage 2 or 3 at 37° C. and 5% $CO_2$. For induction of differentiation NHEKs are seeded in 6-well plates and grown up to confluence and treated with several concentrations of the algae extracts.

Total RNA was isolated using RNeasy Total RNA Kits (Qiagen, Hilden, Germany). The RNA concentration was determined via photometric measurement at 260/280 (Biophotometer, Eppendorf A G, Hamburg, Germany). An aliquot of 100 ng RNA was used for cDNA synthesis. Superscript™ III First-Strand synthesis system for RT-PCR (Invitrogen, Karlsruhe, Germany) was used for the reverse transcription step with random hexamers. For each gene, a specific primer pair was designed by Primer Express™ 2.0 software (Applied Biosystems, Darmstadt, Germany) based on the cDNA sequence published as indicated. The following primer pairs were used:

TABLE 1

Genes and primer pairs used for real time RT-PCR to determine gene expression in Example 3

| Gene | Primer pairs | |
|---|---|---|
| 18S rRNA | 5'-GCCGCTAGAGGTGAAATTCTTG-3' | SEQ ID NO: 1 |
| | 5'-CATTCTTGGCAAATGCTTTCG-3' | SEQ ID NO: 2 |

TABLE 1-continued

Genes and primer pairs used for real time
RT-PCR to determine gene expression in Example 3

| Gene | Primer pairs | |
|---|---|---|
| Transglutaminase-1 | 5'-CCCCCGCAATGAGATCTACA-3' | SEQ ID NO: 3 |
| | 5'-ATCCTCATGGTCCACGTACACA-3' | SEQ ID NO: 4 |
| Involucrin | 5'-CCCATCAGGAGCAAATGAAAC-3' | SEQ ID NO: 5 |
| | 5'-GCTCGACAGGCACCTTCTG-3' | SEQ ID NO: 6 |
| Filaggrin | 5'-AAGGAACTTCTGGAAAAGGAATTTC-3' | SEQ ID NO: 7 |
| | 5'-TTGTGGTCTATATCCAAGTGATCCAT-3' | SEQ ID NO: 8 |
| Loricrin | 5'-TCACATTGCCAGCATCTTCTCT-3' | SEQ ID NO: 9 |
| | 5'-GGCTGCTTTTTCTGATAAGACATCT-3' | SEQ ID NO: 10 |

PCR reactions were carried out on an Opticon 1 (MJ Research, Waltham, Mass., USA) using SYBR Green® PCR Master Mix (Applied Biosystems, Darmstadt, Germany). Each sample was analyzed in double employing the universal protocol over 36 cycles. In detail, 10 minutes 94° C. activation of hot start taq polymerase, 20 seconds 95° C. denaturation, 20 seconds 55° C. annealing, 30 seconds 72° C. extension. For comparison of relative expression in real time PCR control cells and treated cells the 2 (-delta delta C(T)) method was used.

Results

The results of the experiments show an induction of the markers for differentiation in keratinocytes treated with extract no. 1 from coccoid algae. As a known positive control a ceramide mix (10 µM) was used to induce the differentiation markers. For better comparison the keratinocytes have been treated in a second run with the same concentrations based on the protein content of the extracts (8.3 and 0.8 µg/ml). Under these conditions all four markers for induction of keratinocyte differentiation were up-regulated. A ceramide mix was used as a positive control, which induced the markers transglutaminase-1 (TG-1), involucrin (INV), filaggrin (FILA) and loricrin (LORI) to a similar extent.

Figure 1:
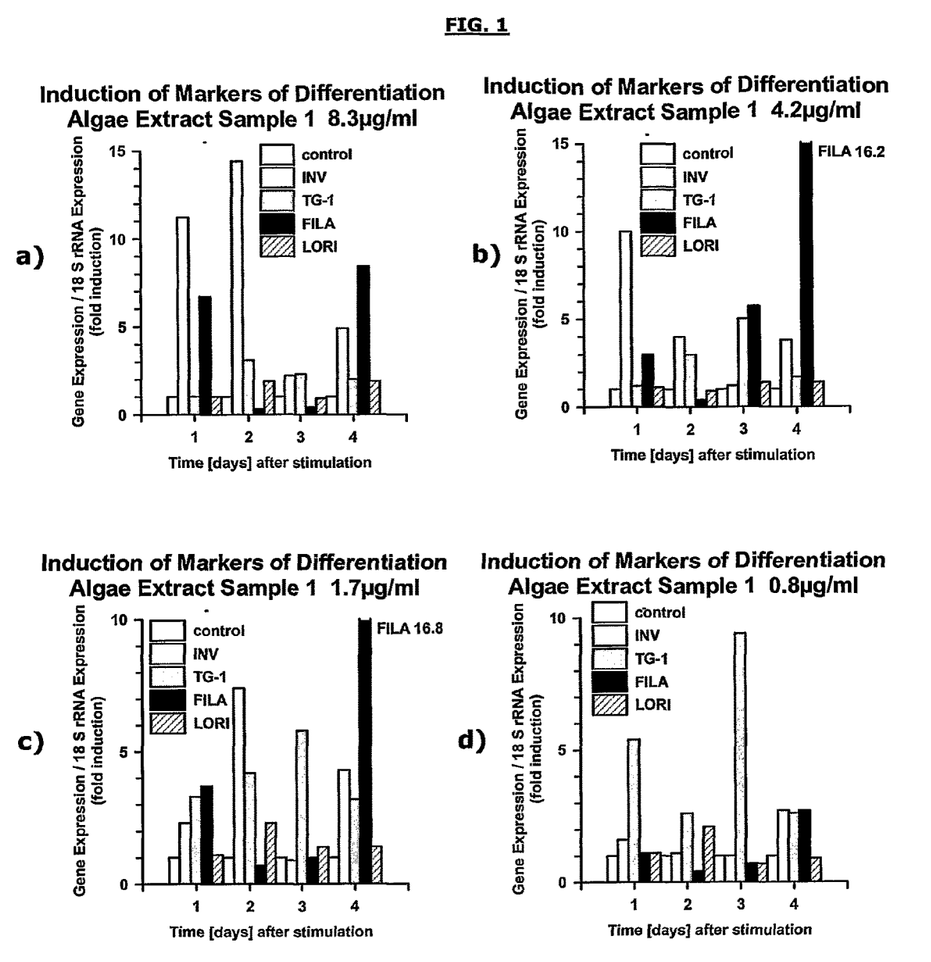
FIG. 1 shows results from Example 3, illustrating the inductive effect of the extract of the coccoid blue-green algae identified as BLICE-0405-01 (accession No. CCAP 1483/1) at varying concentrations on gene expression of human epidermal keratinocytes.
Figure 2:
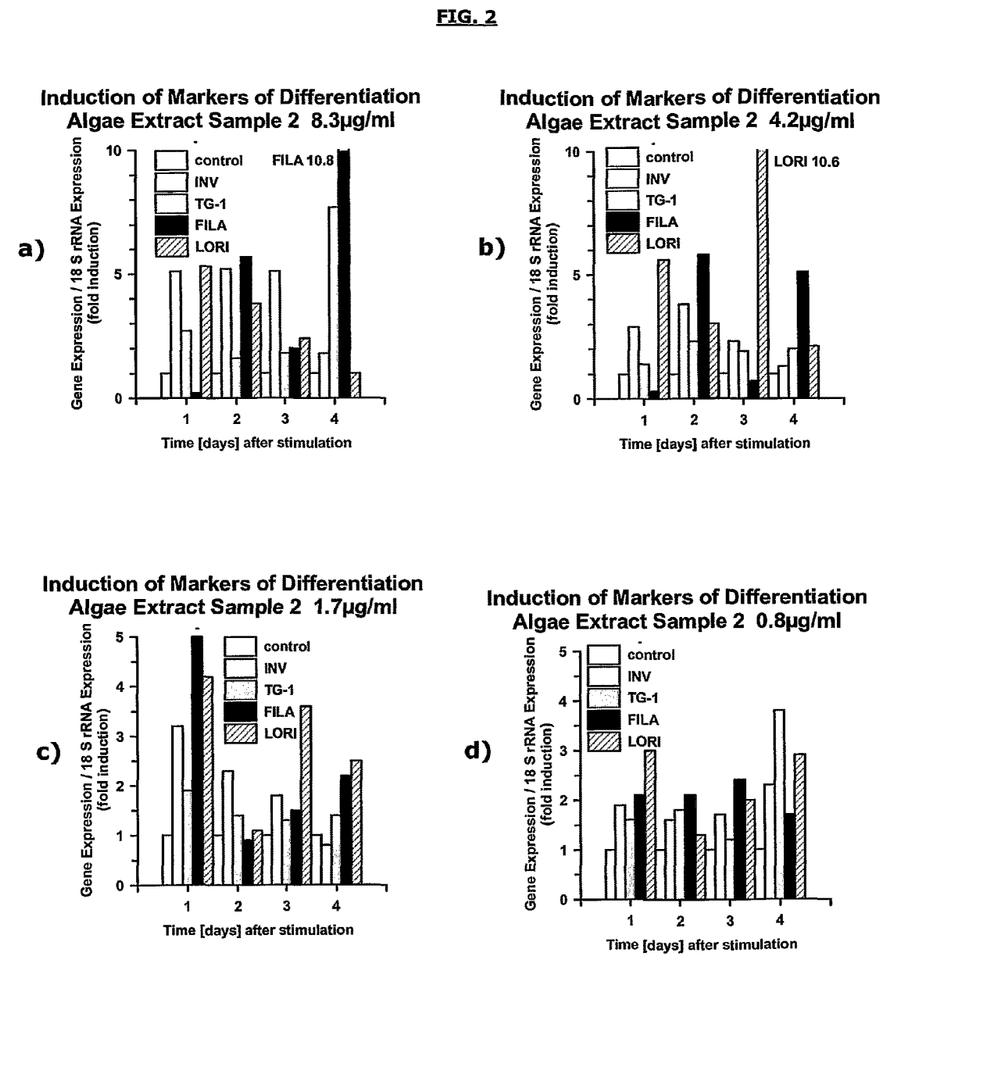
FIG. 2 shows results from Example 3, illustrating the inductive effect of the extract of the filamentous blue-green algae identified as BLICE-0405-02 (accession No. CCAP 1483/2) at varying concentrations on gene expression of human epidermal keratinocytes.

FIGS. 1 and 2 show the expression pattern of transglutaminase-1, involucrin, filaggrin and loricrin, in response to algae extracts 1 and 2; all these genes are markers for skin barrier enhancement as discussed above.

FIG. 1 a-d show induced expression of all four markers in response to algae extract 1 (coccoid algae). The two highest concentrations of the algae extract (panels a and b) show a pronounced increase in expression of all the genes tested, although the loricrin expression was not increased to as great extent as the other genes tested. The gene induction was somewhat dose dependent and different genes were induced at different time points, but it would be expected that genes involved in a differentiation process would be up- and down-regulated at different timepoints. For example, an early induction of the involucrin gene is observed at the higher concentration of both extracts, whereas the filaggrin and the transglutaminase-1 genes have a somewhat later up-regulation.

FIG. 2 a-d show the expression pattern of transglutaminase-1, involucrin, filaggrin and loricrin, in response to filamentous algae extract (extract 2). All four markers are induced in response to the extract and the induction is even more pronounced than what was observed when the cultures were stimulated with the coccoid algae extract (FIG. 1 a-d).

As state of the art reference a ceramide mix was used which induced the markers transglutaminase-1, Involucrin, Filaggrin and Loricrin to a similar extent (not shown).

These results show that both the coccoid and the filamentous algae extracts not only induce terminal differentiation of keratinocytes, but also induce expression of the most important genes in skin barrier enhancement.

Example 4

Photoaging Inhibitory Effect of Algae Extracts

The photoprotective capacity of the algae extracts was assessed in UVA-irradiated human dermal fibroblasts. Induction of MMP-1 is a marker for skin aging. UVA-induced up-regulation of the cytokine IL-6 has previously been shown to be a prerequisite of UVA-induced MMP-1 induction.

Materials and Methods

Human dermal fibroblasts, HDF, prepared from neonatal foreskin are cultured in DMEM supplemented with 10% FBS in 5% $CO_2$ for 4 days until they reached confluence as described (Vielhaber et al., 2006). For all studies, only early passage (<12) fibroblasts will be used to avoid changes in their original phenotype during subculture.

The fibroblasts are incubated with different amount of algae extracts (1 and 2) and subjected to UV light. Briefly, for UVA radiation the medium was replaced by phosphate-buffered saline, lids were removed and cells were exposed to a dose of 30 j/cm$^2$ UVA1 using a UVASUN 24,000 system (Sellas GmbH, Dr. Sellmeier Gevelsberg, Germany). The UVA1 output was determined with a UVAMETER type II (Waldmann, Villingen-Schwenningen, Germany) and found to be approximately 150 mW/cm$^2$ UVA1 at a tube to target distance of 30 cm (Grether-Beck et al. 1996; Grether-Beck et al. 2000). Controls without algae extract are run in parallel. After either 6 or 24 h from UV irradiation, cells are collected and total RNA isolated as described above in Example 3. Quantitative PC is run as described above in Example 3 using specific primer pairs as indicated in Table 2. PCR reactions were carried out as in Example 3.

TABLE 2

Genes and primer pairs used for
real time RT-PCR to determine
gene expression in Example 4

| Gene | Primer Pairs | |
|---|---|---|
| 18S rRNA | 5'-GCCGCTAGAGGTGAAATTCTTG-3' | SEQ ID NO: 1 |
| | 5'-CATTCTTGGCAAATGCTTTCG'-3' | SEQ ID NO: 2 |

TABLE 2-continued

Genes and primer pairs used for
real time RT-PCR to determine
gene expression in Example 4

| Gene | Primer Pairs | |
|---|---|---|
| MMP-1 | 5'-GGGAGATCATCGGGACAACTC-3' | SEQ ID NO: 11 |
| | 5'-GGGCCTGGTTGAAAAGCAT-3' | SEQ ID NO: 12 |
| IL-6 | 5'-AGCCGCCCCACACAGA-3' | SEQ ID NO: 13 |
| | 5'-CCGTCGAGGATGTACCGAAT-3' | SEQ ID NO: 14 |

Results

Figure 3:
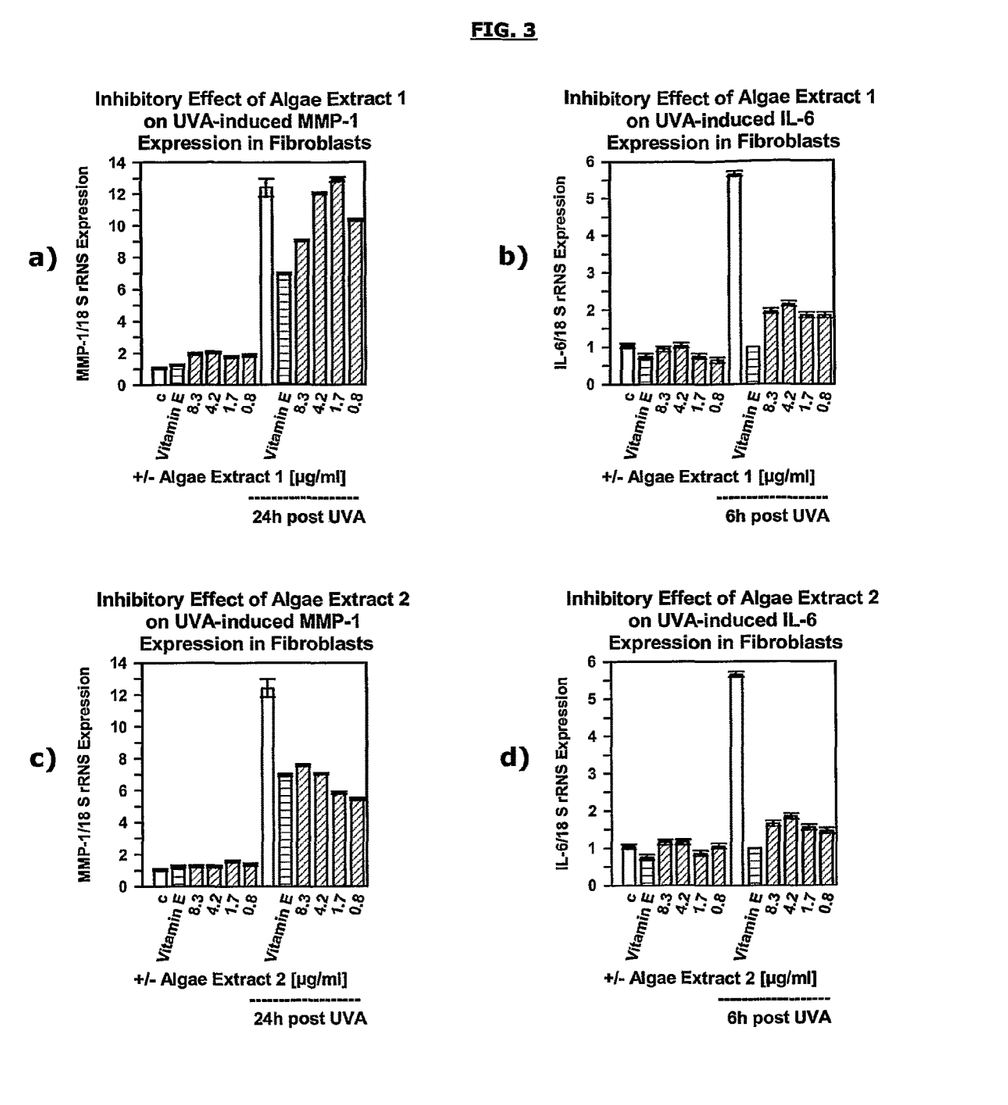
FIG. 3 shows results from Example 4, illustrating the effect of BLICE-0405-01 extracts on MMP-1 expression (top-left), IL-6 expression (top-right), and the effect of BLICE-0405-02 extracts on MMP-1 expression (bottom-left), IL-6 expression (bottom-right) in Fibroblasts.

FIG. 3 shows that the algae extracts (1 and 2) from geothermal sources have an inhibiting effect MMP-1 expression in a dose dependent manner. Algae extract 1 inhibited dose-dependently the UVA-induced up-regulation of MMP-1 (FIGS. 3a and b). In all panels a) though d) left-hand columns show results without UV irradiation and right-hand columns show results after UV irradiation. 'c' indicates control samples with no algae extract added, Vitamin E was also tested as a comparative control.

A closer look at the dose-responses showed that both extracts can inhibit UVA-induced MMP-1 up-regulation: Extract 1 inhibits UVA-induced MMP-1 induction up to 82.7% (2 µg/ml). Extract 2 inhibits UVA-induced MMP-1 up-regulation up to 70.3% (2 µg/ml). These results are in the range of chemical sunscreens. No significant effect of the algae extracts was seen on the expression of IL-6. (FIGS. 3c and d)

The data from the MMP-1 expression analysis strongly indicates that algae extracts (FIGS. 3a and b) both prevent photoaging of the skin by inhibition of UVA-induced MMP-1 expression in human fibroblasts.

Example 5

Skin Enhancement Effect of Algae Extracts—De Novo Collagen Synthesis

The effect of the extracts from Examples 1 and 2 on the on the expression levels of the genes of the Col1A1 and Col1A2 coding for the collagens 1A1 and 1A2.

Materials and Methods

Human dermal fibroblasts, HDF, prepared from neonatal foreskin and cultured for 4 days until they reached confluence as described in Example 2. PCR reactions were carried out as in Example 1 using specific primer pairs as indicated in Table 3.

TABLE 3

Genes and primer pairs used for real time
RT-PCR to determine gene expression in Example 5

| Gene | Primer Pairs | Reference |
|---|---|---|
| 18S rRNA | 5'-GCCGCTAGAGGTGAAATTCTTG-3' | SEQ ID NO: 1 |
| | 5'-CATTCTTGGCAAATGCTTTCG'-3' | SEQ ID NO: 2 |
| Collagen 1A1 | 5'-CCTGCGTGTACCCCACTCA-3' | SEQ ID NO: 15 |
| | 5'-ACCAGACATGCCTCTTGTCCTT-3' | SEQ ID NO: 16 |
| Collagen 1A2 | 5'-GATTGAGACCCTTCTTACTCCTGAA-3' | SEQ ID NO: 17 |
| | 5'-GGGTGGCTGAGTCTCAAGTCA-3' | SEQ ID NO: 18 |

Results

Figure 4:
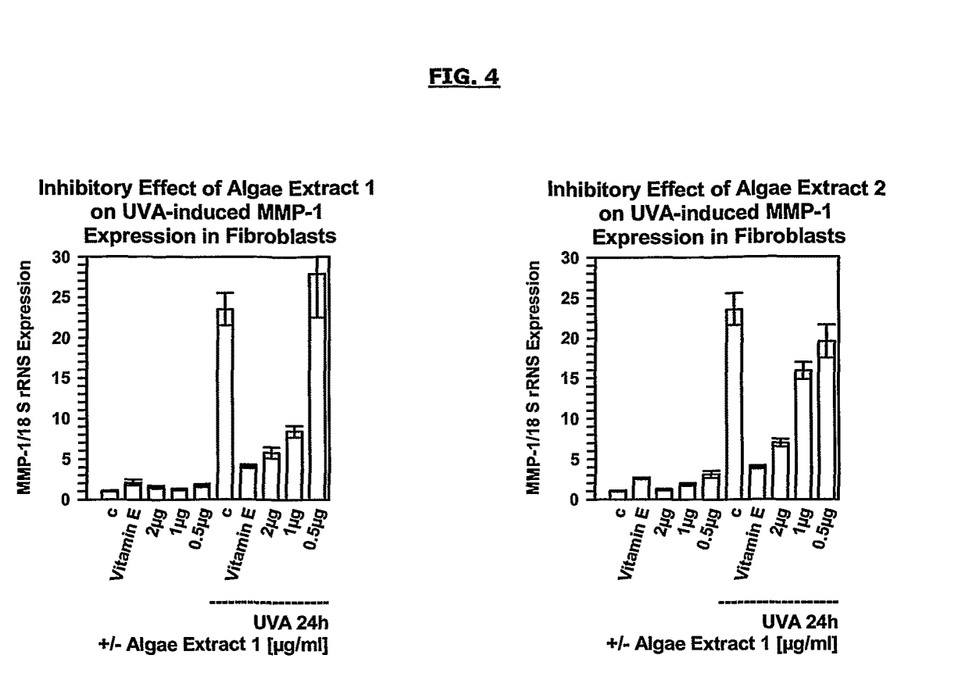
FIG. 4 shows results from Example 5, illustrating the effect of BLICE-0405-01 and BLICE-0405-02 extracts on Collagen 1A1 and Collagen 1A2 gene expression in Fibroblasts.

FIG. 4 shows the capacity of both the coccoid and the filamentous algae extracts to induce the expression of genes coding for the extracellular matrix proteins collagen 1A1 and collagen 1A2. It has shown that induced collagen expression prevents skin aging by inducing skin regeneration through de novo collagen synthesis.

Example 6

Preparation of Formulations with Algae Extract for Cosmetic and/or Pharmaceutical Use The following are examples of different compositions for topical application.

Example 6 (a)

Preparation of a Foaming Product

TABLE 4

| | Ingredients | |
|---|---|---|
| A | Water | 80% |
| A | Sodium laureth sulfate | 10.0% |
| A | Sea water (maris aqua) | 2.0% |
| A | Cocamidopropyl betaine, cocoglucoside | 3.0% |
| A | Sodium chloride | 1.0% |
| A | Glycerin | 0.80% |
| A | Coccoid algae extract (from Ex. 1) | 0.05% |
| A | Filamentous algae extract (from Ex. 2) | 0.45% |
| B | Phenoxyethanol (and) methylparaben (and) ethylparaben (and) propylparaben (and) butylparaben (and) isobutylparaben | 1.0% |
| B | Preservatives, perfume, minor excipients | 1.7% |

Ingredients of phase A are mixed, ingredients of phase B are mixed, and subsequently phase B is added to and mixed with phase A.

Example 6 (b)

Preparation of an Emulsion Product; the Following Ingredients are Mixed

TABLE 5

| | Ingredients | |
|---|---|---|
| A | Water | 77% |
| A | Carbomer | 0.4% |
| B | Hydrogenated vegetable glycerides | 2.5% |
| B | Cetearyl alcohol | 2.0% |

TABLE 5-continued

| | Ingredients | |
|---|---|---|
| B | C6-C10 Fatty acid triglycerides | 2.0% |
| B | Viscosity adjusting agent(s) | 2.5% |
| B | Further emulsifier agent(s) | 3.5% |
| C | Sea water (maris aqua) | 3% |
| C | Glycerin | 1.50% |
| C | Coccoid algae extract (from Ex. 1) | 0.05% |
| C | Filamentous algae extract (from Ex. 2) | 0.45% |
| C | Sodium hydroxide and other pH-adjusters | 0.75% |
| D | Phenoxyethanol (and) methylparaben (and) ethylparaben (and) propylparaben (and) butylparaben (and) isobutylparaben | 1.0% |
| D | Other preservatives, perfume, other minor excipients | 1.3% |
| E | Aluminum starch octenyl succinate | 2.0% |

Ingredients A are mixed at 70° C., ingredients B are mixed at and added to phase A. ingredients C are added in the order shown to the mix at 45° C., ingredients D are added at 40° C. and ingredients E are added at 35° C.

Example 6 (c)

Preparation of a Lotion; the Following Ingredients are Mixed

TABLE 6

| | Ingredients | |
|---|---|---|
| A | Water | 89% |
| B | Sea water (maris aqua) | 2.7% |
| B | Glycerin | 2.5% |
| B | Soodium PCA | 0.60% |
| B | Coccoid algae extract (from Ex. 1) | 0.03% |
| B | Filamentous algae extract (from Ex. 2) | 0.45% |
| B | Sodium hydroxide (and other pH-adjusters) | 0.25% |
| C | PEG-40 hydrogenated castor oil | 0.70% |
| C | Polysorbate (and) benzoic acid | 0.50% |
| C | Phenoxyethanol (and) methylparaben (and) ethylparaben (and) propylparaben (and) butylparaben (and) isobutylparaben | 1.0% |
| C | Other preservatives, perfume, other minor excipients, coloring agents, etc. | 1.17% |

Ingredients of A phase are mixed, ingredients B are added thereto, ingredients C are mixed together and added to the A + B mixture.
Ingredients A are mixed at 70° C., ingredients B are mixed at and added to phase A. ingredients C are added in the order shown to the mix at 45° C., ingredients D are added at 40° C. and ingredients E are added at 35° C.

Example 6 (d)

Preparation of Powder Product; the Following Ingredients are Mixed

TABLE 7

| | Ingredients | |
|---|---|---|
| A | Talc | 81.5% |
| B | dimethicone | 1.0% |
| B | kaolin | 9% |
| B | *Oriza sativa* starch | 2.0% |
| C | Talc | 5.0% |
| C | Coccoid algae extract (from Ex. 1) | 0.03% |
| C | Filamentous algae extract (from Ex. 2) | 0.45% |
| C | preservatives, perfume, anti-coagulant, other minor excipients | 1.02% |

Ingredients B are added to A, ingredients C are mixed together and added to the A + B mix.

Example 7

Preparation of Formulations with Algae Extract and Bioactive Silica for Cosmetic and/or Pharmaceutical Use The following are examples of different compositions for topical application.

Example 7 (a)

Preparation of a Foaming Product

TABLE 8

| | Ingredients | |
|---|---|---|
| A | Water | 80% |
| A | Sodium laureth sulfate | 10.0% |
| A | Sea water (maris aqua) | 2.0% |
| A | Cocamidopropyl betaine, cocoglucoside | 3.0% |
| A | Sodium chloride | 1.0% |
| A | Glycerin | 0.80% |
| A | Coccoid algae extract (from Ex. 1) | 0.05% |
| A | Filamentous algae extract (from Ex. 2) | 0.45% |
| A | Silica mud | 0.12% |
| B | Phenoxyethanol (and) methylparaben (and) ethylparaben (and) propylparaben (and) butylparaben (and) isobutylparaben | 1.0% |
| B | Preservatives, perfume, minor excipients | 1.58% |

Ingredients of phase A are mixed, ingredients of phase B are mixed, and subsequently phase B is added to and mixed with phase A.

Example 7 (b)

Preparation of an Emulsion Product; the Following Ingredients are Mixed

TABLE 9

| | Ingredients | |
|---|---|---|
| A | Water | 77% |
| A | Carbomer | 0.4% |
| B | Hydrogenated vegetable glycerides | 2.5% |
| B | Cetearyl alcohol | 2.0% |
| B | C6-C10 Fatty acid triglycerides | 2.0% |
| B | Viscosity adjusting agent(s) | 2.5% |
| B | Further emulsifier agent(s) | 3.5% |
| C | Sea water (maris aqua) | 3% |
| C | Glycerin | 1.50% |
| C | Coccoid algae extract (from Ex. 1) | 0.05% |
| C | Filamentous algae extract (from Ex. 2) | 0.45% |
| C | Silica mud | 0.12% |
| C | Sodium hydroxide and other pH-adjusters | 0.75% |
| D | Phenoxyethanol (and) methylparaben (and) ethylparaben (and) propylparaben (and) butylparaben (and) isobutylparaben | 1.0% |
| D | Other preservatives, perfume, other minor excipients | 1.18% |
| E | Aluminum starch octenyl succinate | 2.0% |

Ingredients A are mixed at 70° C., ingredients B are mixed at and added to phase A. ingredients C are added in the order shown to the mix at 45° C., ingredients D are added at 40° C. and ingredients E are added at 35° C.

Example 7 (c)

Preparation of a Lotion; the Following Ingredients are Mixed

TABLE 10

| | Ingredients | |
|---|---|---|
| A | Water | 89% |
| B | Sea water (maris aqua) | 2.7% |
| B | Glycerin | 2.5% |
| B | Sodium PCA | 0.60% |
| B | Coccoid algae extract (from Ex. 1) | 0.03% |
| B | Filamentous algae extract (from Ex. 2) | 0.45% |
| B | Sodium hydroxide (and other pH-adjusters) | 0.25% |
| C | PEG-40 hydrogenated castor oil | 0.70% |
| C | Polysorbate (and) benzoic acid | 0.50% |
| C | Phenoxyethanol (and) methylparaben (and) ethylparaben (and) propylparaben (and) butylparaben (and) isobutylparaben | 1.0% |
| C | Other preservatives, perfume, other minor excipients, coloring agents, etc. | 1.17% |

Ingredients of A phase are mixed, ingredients B are added thereto, ingredients C are mixed together and added to the A + B mixture.
Ingredients A are mixed at 70° C., ingredients B are mixed at and added to phase A. ingredients C are added in the order shown to the mix at 45° C., ingredients D are added at 40° C. and ingredients E are added at 35° C.

Example 7 (d)

Preparation of Powder Product; the Following Ingredients are Mixed

TABLE 11

| | Ingredients | |
|---|---|---|
| A | Talc | 81.5% |
| B | dimethicone | 1.0% |
| B | kaolin | 9% |

TABLE 11-continued

| | Ingredients | |
|---|---|---|
| B | *Oriza sativa* starch | 2.0% |
| C | Talc | 5.0% |
| C | Coccoid algae extract (from Ex. 1) | 0.03% |
| C | Filamentous algae extract (from Ex. 2) | 0.45% |
| C | preservatives, perfume, anti-coagulant, other minor excipients | 1.02% |

Ingredients B are added to A, ingredients C are mixed together and added to the A + B mix.

REFERENCES

1. Chung K-Y., et al. An AP-1 binding sequence is essential for regulation of the human α2(I) collagen (COL1A2) promoter activity by transforming growth factor-β. *J. Biol. Chem.* 271: 3272-3278, 1996.
2. Grether-Beck S., et al. Activation of transcription factor AP-1 mediates UVA radiation and singlet oxygen-induced expression of the human intercellular adhesion molecule 1 gene. *Proc. Nat. Acad. Sci. USA.* 93: 14586-14591, 1996.
3. Grether-Beck S., et al. Mitochondrial Cytochrome c Release mediates ceramide-induced activator protein 2 activation and gene expression in keratinocytes. *J. Biol. Chem.* 278: 47498-47507, 2003.
4. Scharffetter K., et al. UVA irradiation induces collagenase in human dermal fibroblasts in vitro and in vivo. *Arch. Dermatol. Res.* 283: 506-511, 1991.
5. Südel K. M., et al. Novel Aspects of Intrinsic and Extrinsic Aging of Human Skin: Beneficial Effects of Soy Extract. *Photochem. Photobiol.* 81: 581-587, 2005.
6. Vielhaber G., et al. Sunscreens with an absorption maximum of ≥360 provide optimal protection against UVA1-induced expression of matrix metalloproteinase-1, interleukin-1, and interleukin-6 in human dermal fibroblasts. *Photochem. Photobiol. Sci.* 5: 275-282, 2006.

The invention claimed is:

1. A pharmaceutical or cosmetic composition comprising supernatant of centrifuged ruptured cells of blue-green algae, wherein said algae are selected from the group consisting of species having a 16S rRNA sequence of SEQ ID NO: 19, and a 16S rRNA sequence of SEQ ID NO: 20.

2. A pharmaceutical or cosmetic composition comprising supernatant of centrifuged ruptured cells of blue-green algae, wherein said algae comprise *Cyanobacterium* sp. deposited with the Culture Collection of Algae and Protozoa SAMS Research Services Ltd., United Kingdom, under Accession No. CCAP 1483/1.

3. A pharmaceutical or cosmetic composition comprising supernatant of centrifuged ruptured cells of blue-green algae, wherein said algae comprise *Cyanobacterium* sp. deposited with the Culture Collection of Algae and Protozoa SAMS Research Services Ltd., United Kingdom, under Accession No. CCAP 1483/2.

4. The pharmaceutical or cosmetic composition of claim 1, which is in a form selected from the group consisting of a lotion, a cream, an emulsion, a paste, a gel, an ointment, an anhydrous base, a suspension.

5. A topical or cosmetic composition comprising a supernatant of centrifuged ruptured cells of blue-green algae that grow in a saline hot water source, and at least one pharmaceutically or cosmetically acceptable carrier or diluents, wherein said algae are selected from the group consisting of species having a 16S rRNA sequence of SEQ ID NO: 19, and a 16S rRNA sequence of SEQ ID NO: 20.

6. A topical or cosmetic composition comprising a supernatant of centrifuged ruptured cells of blue-green algae that grow in a saline hot water source, and at least one pharmaceutically or cosmetically acceptable carrier or diluents, wherein said algae comprise *Cyanobacterium* sp. deposited with the Culture Collection of Algae and Protozoa SAMS Research Services Ltd., United Kingdom, under Accession No. CCAP 1483/2.

7. A topical or cosmetic composition comprising a supernatant of centrifuged ruptured cells of blue-green algae that grow in a saline hot water source, and at least one pharmaceutically or cosmetically acceptable carrier or diluents, wherein said algae comprise *Cyanobacterium* sp. deposited with the Culture Collection of Algae and Protozoa SAMS Research Services Ltd. United Kingdom.

8. The composition of claim 5, which is in a form selected from the group consisting of a fatty or non-fatty cream, a milky suspension or emulsion of the water-in-oil or oil-in-water type, a lotion, a gel or jelly, a colloidal or non- colloidal aqueous or oily solution, a paste, a soap, a foam, an anhydrous base including a powder, an ointment, a semi-soluble or dispersible tablet and a stick.

9. The composition of claim 5, further comprising silica.

10. The composition of claim 9, wherein said silica is precipitated from natural saline hot water sources.

11. The composition of claim 9, wherein said silica is obtainable from diatoms.

12. The composition of claim 9, where said silica is in a colloidal form.

13. The pharmaceutical or cosmetic composition of claim 2, which is in a form selected from the group consisting of a lotion, a cream, an emulsion, a paste, a gel, an ointment, an anhydrous base, a suspension.

14. The pharmaceutical or cosmetic composition of claim 3, which is in a form selected from the group consisting of a lotion, a cream, an emulsion, a paste, a gel, an ointment, an anhydrous base, a suspension.

15. The composition of claim 6, which is in a form selected from the group consisting of a fatty or non-fatty cream, a milky suspension or emulsion of the water-in-oil or oil-in-water type, a lotion, a gel or jelly, a colloidal or non- colloidal aqueous or oily solution, a paste, a soap, a foam, an anhydrous base including a powder, an ointment, a semi-soluble or dispersible tablet and a stick.

16. The composition of claim 6, further comprising silica.

17. The composition of claim 7, which is in a form selected from the group consisting of a fatty or non-fatty cream, a milky suspension or emulsion of the water-in-oil or oil-in-water type, a lotion, a gel or jelly, a colloidal or non-colloidal aqueous or oily solution, a paste, a soap, a foam, an anhydrous base including a powder, an ointment, a semi-soluble or dispersible tablet and a stick.

18. The composition of claim 7, further comprising silica.

19. The pharmaceutical or cosmetic composition of claim 1, consisting of supernatant of centrifuged, ruptured cells of blue-green algae, wherein said algae are selected from the group consisting of species having a 16S rRNA sequence of SEQ ID NO: 19, and a 16S rRNA sequence of SEQ ID NO: 20.

20. The pharmaceutical or cosmetic composition of claim 2, consisting of supernatant of centrifuged, ruptured cells of blue-green algae, wherein said algae comprise *Cyanobacterium* sp. deposited with the Culture Collection of Algae and Protozoa SAMS Research Services Ltd., United Kingdom, under Accession No. CCAP 1483/1.

21. The pharmaceutical or cosmetic composition of claim 3, consisting of supernatant of centrifuged ruptured cells of blue-green algae, wherein said algae comprise *Cyanobacterium* sp. deposited with the Culture Collection of Algae and Protozoa SAMS Research Services Ltd., United Kingdom, under Accession No. CCAP 1483/2.

\* \* \* \* \*

UNITED STATES PATENT AND TRADEMARK OFFICE
CERTIFICATE OF CORRECTION

PATENT NO. : 8,795,679 B2  
APPLICATION NO. : 12/299749  
DATED : August 5, 2014  
INVENTOR(S) : Sigurbjorn Einarsson et al.

Page 1 of 1

It is certified that error appears in the above-identified patent and that said Letters Patent is hereby corrected as shown below:

In the Claims

Column 27, Line 19 currently reads:

Research Services Ltd. United Kingdom.

And should read:

Research Services Ltd. United Kingdom, under Accession No. CCAP 1483/2.

Signed and Sealed this
Twenty-seventh Day of January, 2015

Michelle K. Lee
*Deputy Director of the United States Patent and Trademark Office*

SEQUENCE LISTING

```
<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
gccgctagag gtgaaattct tg                                                  22

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
cattcttggc aaatgctttc g                                                   21

<210> SEQ ID NO 3
<211> LENGTH: 20
<212> TYPE: DNA
<213> ORGANISM: Artificial Sequence
<220> FEATURE:
```

```
<223> OTHER INFORMATION: synthetic primer

<400> SEQUENCE: 3
cccccgcaat gagatctaca                                                  20

<210> SEQ ID NO 4
<211> LENGTH: 22
<212> TYPE: DNA
<213> ORGANISM: Artificial Sequence
<220> FEATURE:
<223> OTHER INFORMATION: synthetic primer

<400> SEQUENCE: 4
atcctcatgg tccacgtaca ca                                               22

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
cccatcagga gcaaatgaaa c                                                21

<210> SEQ ID NO 6
<211> LENGTH: 19
<212> TYPE: DNA
<213> ORGANISM: Artificial Sequence
<220> FEATURE:
<223> OTHER INFORMATION: synthetic primer

<400> SEQUENCE: 6
gctcgacagg caccttctg                                                   19

<210> SEQ ID NO 7
<211> LENGTH: 25
<212> TYPE: DNA
<213> ORGANISM: Artificial Sequence
<220> FEATURE:
<223> OTHER INFORMATION: synthetic primer

<400> SEQUENCE: 7
aaggaacttc tggaaaagga atttc                                            25

<210> SEQ ID NO 8
<211> LENGTH: 26
<212> TYPE: DNA
<213> ORGANISM: Artificial Sequence
<220> FEATURE:
<223> OTHER INFORMATION: synthetic primer

<400> SEQUENCE: 8
ttgtggtcta tatccaagtg atccat                                           26

<210> SEQ ID NO 9
<211> LENGTH: 22
<212> TYPE: DNA
<213> ORGANISM: Artificial Sequence
<220> FEATURE:
<223> OTHER INFORMATION: synthetic primer

<400> SEQUENCE: 9
tcacattgcc agcatcttct ct                                               22
```

```
<210> SEQ ID NO 10
<211> LENGTH: 25
<212> TYPE: DNA
<213> ORGANISM: Artificial Sequence
<220> FEATURE:
<223> OTHER INFORMATION: synthetic primer

<400> SEQUENCE: 10
ggctgctttt tctgataaga catct                                        25

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
gggagatcat cgggacaact c                                            21

<210> SEQ ID NO 12
<211> LENGTH: 19
<212> TYPE: DNA
<213> ORGANISM: Artificial Sequence
<220> FEATURE:
<223> OTHER INFORMATION: synthetic primer

<400> SEQUENCE: 12
gggcctggtt gaaaagcat                                               19

<210> SEQ ID NO 13
<211> LENGTH: 16
<212> TYPE: DNA
<213> ORGANISM: Artificial Sequence
<220> FEATURE:
<223> OTHER INFORMATION: synthetic primer

<400> SEQUENCE: 13
agccgcccca cacaga                                                  16

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
ccgtcgagga tgtaccgaat                                              20

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
cctgcgtgta ccccactca                                               19

<210> SEQ ID NO 16
<211> LENGTH: 22
<212> TYPE: DNA
<213> ORGANISM: Artificial Sequence
<220> FEATURE:
<223> OTHER INFORMATION: synthetic primer
```

<400> SEQUENCE: 16
accagacatg cctcttgtcc tt                                             22

<210> SEQ ID NO 17
<211> LENGTH: 25
<212> TYPE: DNA
<213> ORGANISM: Artificial Sequence
<220> FEATURE:
<223> OTHER INFORMATION: synthetic primer

<400> SEQUENCE: 17
gattgagacc cttcttactc ctgaa                                          25

<210> SEQ ID NO 18
<211> LENGTH: 21
<212> TYPE: DNA
<213> ORGANISM: Artificial Sequence
<220> FEATURE:
<223> OTHER INFORMATION: synthetic primer

<400> SEQUENCE: 18
gggtggctga gtctcaagtc a                                              21

<210> SEQ ID NO 19
<211> LENGTH: 1430
<212> TYPE: DNA
<213> ORGANISM: Cyanobacterium sp.

<400> SEQUENCE: 19
gagtttgatc ctggctcagg atgaacgctg gcggtatgcc taacacatgc aagtcgaacg      60
ggctcttcgg agctagtggc ggacgggtga ggaacgcgtg agaacctgcc tcaaggtcgg     120
ggacaacagt tggaaacgac tgctaatacc ggatgagccg aataggtaaa agatttatcg     180
cctagagagg ggctcgcgtc tgattagcta gatggtgagg taaaggctta ccatggcgac     240
gatcagtagc tggtctgaga ggatgagcag ccacactggg actgagacac ggcccagact     300
cctacgggag gcagcagtgg ggaattttcc gcaatgggcg aaagcctgac ggagcaatac     360
cgcgtgaggg aggaaggctc ttgggttgta aacctcaaaa cttagggaag aaaaaaatga     420
cggtacctaa tgtaagcatc ggctaactcc gtgccagcag ccgcggtaat acggaggatg     480
caagcgttat ccggaatcat tgggcgtaaa gagtccgtag gtggcacttc aagtctgctt     540
tcaaagaccg aagctcaact tcggaaaggg agtggaaact gaagagctag agtatagtag     600
gggtagaggg aattcctagt gtagcggtga aatgcgtaga gattaggaag aacaccagtg     660
gcgaaggcgc tctactgggc atatactgac actgagggac gaaagctagg ggagcgaaag     720
ggattagata cccctgtagt cctagcggta acgatggat actaggcgta gtgctgttag     780
aaggactgtg ccgaagctaa cgcgttaagt atcccgcctg gggagtacgc acgcaagtgt     840
gaaactcaaa ggaattgacg ggacccgcca agcggtgg agtatgtggt ttaattcgat     900
gcaacgcgaa gaaccttacc aaggcttgac atcctgcgaa tcttggagaa atctgagagt     960
gcctaaggga acgcagagac aggtggtgca tggctgtcgt cagctcgtgt cgtgagatgt    1020
tgggttaagt cccgcaacga gcgcaaccct cgtccttagt tgccagcatt aagttgggga    1080
ctctagggag accgccgggg agaactcgga ggaaggtggg gatgacgtca agtcagcatg    1140 cccttacgt cttgggctac acacgtacta caatggttgg gacaaagggg agcgaaaccg    1200
cgaggtggag cgaatctcat caaacccagc cacagttcag attgcagtct gaaactcgcc    1260
tgcatgaagg aggaatcgct agtaatcgca ggtcagcata ttgcggtgaa tccgttcccg    1320

```
ggtcttgtac acaccgcccg tcacaccatg gaagttggtc acgcccgaag tcgttattct    1380
aacccaagtg aaggagacg ccgaaggtgg gactagtgac tggggtgaag              1430

<210> SEQ ID NO 20
<211> LENGTH: 1448
<212> TYPE: DNA
<213> ORGANISM: Cyanobacterium sp.

<400> SEQUENCE: 20
gagtttgatc ctggctcagg atgaacgctg gcggtctgct taacacatgc aagtcgaacg     60
gagtgcttcg gcacttagtg gcggacgggt gagtaacgcg tgagaatctg cccttaggag    120
ggggataacg actggaaacg gtcgctaaga ccccatatgc cgagaggtga aacagttttc    180
tgcctgagga tgagctcgcg tctgattagc tagttggtgg ggtaagagcc taccaaggcg    240
acgatcagta gctggtctga gaggatgacc agccacactg ggactgagac acggcccaga    300
ctcctacggg aggcagcagt ggggaatttt ccgcaatggg cgaaagcctg acggagcaag    360
accgcgtggg ggaagaaggt ctgtggattg taaacctctt ttgaccggga agaagcctga    420
cggtaccggt cgaatcagcc tcggctaact ccgtgccagc agccgcggta atacggagga    480
ggcaagcgtt atccggaatt attgggcgta aagcgtccgc aggtggttta tcaagtcagc    540
tgttaagggg tggggcttaa ctccataaag gcagttgaaa ctgataggct agagtgcgat    600
aggggcaagg ggaattccca gtgtagcggt gaaatgcgta gatattggga agaacaccgg    660
tggcgaaagc gccttgctgg gtctgcactg acactgaggg acgaaagcta ggggagcgaa    720
agggattaga taccctgta gtcctagctg taaacgatgg gtactaggcg ttgtccgtat    780
cgacccgggc agtgccgtag ctaacgcgtt aagtaccccg cctggggagt acgctcgcaa    840
gagtgaaact caaaggaatt gacggggcc cgcacaagcg gtggagtatg tggtttaatt    900
cgatgcaacg cgaagaacct taccaggggtt tgacatgtcc ggaatcttct tgaaagggaa    960
gagtgcctac gggaaccgga acacaggtgg tgcatggctg tcgtcagctc gtgtcgtgag    1020
atgttgggtt aagtcccgca acgagcgcaa cccacgtcct tagttgccag cattgagttg    1080
ggcactctgg ggagactgcc ggtgacaaac cggaggaagg tgtggatgac gtcaagtcag    1140
catgcccctt acgctctggg ctacacacgt actacaatgc ttcggacaaa gggttgccaa    1200
ctcgcgagag tgcgctaatc ccataaaccg aggctcagtt cagattgcag gctgcaactc    1260
gcctgcatga aggcggaatc gctagtaatc gcaggtcagc atactgcggt gaatacgttc    1320
ccgggccttg tacaccgc ccgtcacacc atggagttg gccacgcccg aagtcgttac    1380
tccaaccgat tctgtcggag gaggatgccg aaggcagggc tgatgactgg ggtgaagtcg    1440
taatcaag                                                           1448
```